US012708492B2

(12) United States Patent
Lee et al.

(10) Patent No.: US 12,708,492 B2
(45) Date of Patent: Aug. 18, 2026

(54) DIGITAL SCAN BODY ALIGNMENT METHOD AND DEVICE USING THE SAME

(71) Applicant: MEDIT CORP., Seoul (KR)

(72) Inventors: Dong Hoon Lee, Goyang-si (KR); Won Hoon Choi, Seoul (KR); Dong Hwa Kang, Seoul (KR)

(73) Assignee: MEDIT CORP., Seoul (KR)

( * ) Notice: Subject to any disclaimer, the term of this patent is extended or adjusted under 35 U.S.C. 154(b) by 1119 days.

(21) Appl. No.: 17/472,592

(22) Filed: Sep. 11, 2021

(65) Prior Publication Data

US 2021/0401549 A1 Dec. 30, 2021

Related U.S. Application Data

(63) Continuation of application No. PCT/KR2020/003479, filed on Mar. 12, 2020.

(30) Foreign Application Priority Data

Mar. 12, 2019 (KR) ........................ 10-2019-0028136
Mar. 12, 2020 (KR) ........................ 10-2020-0030767

(51) Int. Cl.
*A61C 8/00* (2006.01)
*A61C 9/00* (2006.01)
(Continued)

(52) U.S. Cl.
CPC .......... *A61C 8/0001* (2013.01); *A61C 9/0053* (2013.01); *G06T 7/0014* (2013.01);
(Continued)

(58) Field of Classification Search
None
See application file for complete search history.

(56) References Cited

U.S. PATENT DOCUMENTS

2012/0135371 A1 5/2012 Jahn
2014/0234801 A1* 8/2014 Herrington ........ A61C 13/0004 703/1

(Continued)

FOREIGN PATENT DOCUMENTS

JP 2006-500999 A 1/2006
JP 2012-139540 A 7/2012

(Continued)

OTHER PUBLICATIONS

International Search Report mailed Jun. 29, 2020 for International Application No. PCT/KR2020/003479 and its English translation.

(Continued)

*Primary Examiner* — Jeffrey J Chow

(57) ABSTRACT

The present invention relates to a digital scan body alignment method and a device using the same. The present invention corrects scan data through library data corresponding to image data on oral structure. At that time, to achieve best-fit of aligning the library data to the scan data initially, the data alignment can be performed by using a first alignment step. In order to accomplish data correction by more accurate data alignment, a second alignment step can be performed using the library data which includes shape information and axis information. By performing the second alignment step, corrected data having higher reliability can be formed, and a more precise prosthesis can be provided to a patient.

21 Claims, 7 Drawing Sheets

(51) Int. Cl.

| | |
|---|---|
| ***G06T 7/00*** | (2017.01) |
| ***G06T 7/30*** | (2017.01) |
| ***G06T 15/08*** | (2011.01) |
| ***G06V 30/142*** | (2022.01) |
| ***G16H 30/40*** | (2018.01) |

(52) U.S. Cl.

CPC ................ *G06T 7/30* (2017.01); *G06T 15/08* (2013.01); *G16H 30/40* (2018.01); *G06T 2200/04* (2013.01); *G06T 2200/24* (2013.01); *G06T 2207/30036* (2013.01); *G06V 30/142* (2022.01)

(56) References Cited

U.S. PATENT DOCUMENTS

| | | | | |
|---|---|---|---|---|
| 2014/0377714 | A1 | 12/2014 | Jahn | |
| 2016/0346065 | A1 | 12/2016 | Chung | |
| 2018/0005371 | A1* | 1/2018 | Sabina | A61C 13/0004 |
| 2018/0193114 | A1 | 7/2018 | Entelis | |
| 2021/0192759 | A1* | 6/2021 | Lang | A61B 90/98 |
| 2022/0168074 | A1* | 6/2022 | Bogdanic | G16H 30/40 |

FOREIGN PATENT DOCUMENTS

| | | | |
|---|---|---|---|
| KR | 10-2015-0108535 | A | 9/2015 |
| KR | 10-2015-0108535 | B1 | 9/2015 |
| KR | 10-1631258 | B1 | 6/2016 |
| KR | 10-1632378 | B1 | 6/2016 |

OTHER PUBLICATIONS

Notice of Allowance mailed Oct. 18, 2022 for Korean Application No. 10-2020-0030767.

Extended European Search Report mailed Nov. 25, 2022 for European Application No. 20771031.0.

* cited by examiner

DIGITAL SCAN BODY ALIGNMENT METHOD AND DEVICE USING THE SAME

CROSS-REFERENCE TO RELATED APPLICATIONS

This application is a continuation application of International Application No. PCT/KR2020/003479, filed Mar. 12, 2020, which claims the benefit of Korean Patent Application Nos. 10-2019-0028136, filed Mar. 12, 2019, and 10-2020-0030767, filed Mar. 12, 2020, in the Korean Intellectual Property Office, the disclosures of which are incorporated herein in their entirety by reference.

TECHNICAL FIELD

The present disclosure relates to a method for aligning a digital scanbody and a device using the same, and more particularly, to a method for aligning a digital scanbody, which generates a digital scanbody whose location is aligned on the basis of the shape information of a library for the scanbody, and a device using the same.

BACKGROUND ART

In general, the teeth of a person enable the person to chew food, such that the food can be easily digested, and play an important role in pronunciation. When such teeth are abnormal, the states of the teeth need to be diagnosed and treated. If necessary, artifacts are implanted in place of the respective teeth. In general, when a tooth is lost, an artificial tooth is implanted through a tooth implant procedure. During the implant procedure, it is important to implement the same impression model as the inside of the oral cavity of a patient.

Conventionally, an impression model has been created to fabricate a prosthesis. In this case, an impression material might be deformed to make it difficult to precisely fabricate a prosthesis. Furthermore, the impression model could not be repeatedly acquired due to the deformation or loss of the impression model. Therefore, in order to overcome the problem of the impression model, a method for fabricating an implant prosthesis using a 3D scanner is actively used in recent years.

In order to fabricate an implant prosthesis, 3D scan data including a physical scanbody through the 3D scanner are acquired. Then, the 3D scan data are aligned through a scanbody design file stored in software, i.e. a scanbody library, and the location of an implant fixture is checked through the aligned 3D scan data.

Therefore, in order to check the location of the fixture, the 3D scan data and the shape information of the scanbody library stored in the software need to be accurately aligned with each other.

As a method for aligning the scan data and the scanbody library, a best-fit algorithm is used. The best-fit algorithm is to minimize a deviation error by adjusting the location of a target to be aligned, by using a deviation minimization option.

In the related art, however, a scan error may occur during a scan process for acquiring scan data. Furthermore, since no weight is given to a central axis, a rotation direction or the like, which is important information of the scanbody, during the alignment process, it is difficult to secure precision required for an actual procedure, while the entire error is only reduced.

DISCLOSURE

Technical Problem

Various embodiments are directed to a method for aligning a digital scanbody, which can generate a corrected scanbody by performing alignment on the basis of the shape information and axis information of scan data acquired through a scanner.

Also, various embodiments are directed to a device for aligning a digital scanbody, which uses the above-described method for aligning a digital scanbody, based on the shape information and axis information of the scan data.

The technical problems of the present disclosure are not limited to the above-described problems, and other technical problems which are not described will be clearly understood by those skilled in the art, based on the following descriptions.

Technical Solution

In an embodiment, a method for aligning a digital scanbody may include: a library data selection step of selecting one or more library data among a plurality of library model data stored in a library; an image acquisition step of acquiring image data by scanning an oral structure including a structure through a scanner; and an alignment step of aligning the image data and the library data.

The image data acquired in the image acquisition step may be three-dimensional (3D) scan data acquired through the scan.

The library data may be data on a scanbody which is to be implanted into an oral cavity.

The method may further include arranging the library data, selected in the library data selection step, at a random location on a user interface.

The library data arranged at the random location on the user interface may include shape information and axis information.

The alignment step may include performing the alignment by matching shape information and axis information of the scan data on the structure, acquired in the image acquisition step, with shape information and axis information of the library data.

The alignment step may include one or more alignment steps.

The alignment step may include a first alignment step of aligning the image data and the library data by using a best-fit algorithm.

The alignment step may further include a second alignment step of aligning the image data and the library data by using an algorithm different from the first alignment step.

The second alignment step may include performing additional alignment by matching shape information and axis information of the scan data on the structure, acquired in the image acquisition step, with shape information and axis information of the library data.

The method may further include a reliability check step of determining whether an error between the library data and the scan data acquired from the image data is equal to or less than a preset value, after the second alignment step.

The reliability check step may include performing additional alignment when the error between the library data and the scan data exceeds the preset value, and generating a corrected scan body on the basis of the aligned data when the error between the library data and the scan data is equal to or less than the preset value.

In an embodiment, a method for aligning a digital scanbody may include: an image acquisition step of acquiring image data by scanning an oral structure including a structure through a scanner; a data selection step of selecting one or more library data among a plurality of library model data stored in a library; and an alignment step of aligning the image data and the library data.

Model information including shape information and axis information may be acquired from the scan data on the structure, acquired in the image acquisition step.

The method may further include selectively searching for library data corresponding to the model information on the structure.

The method may further include selecting one or more library data among a plurality of library model data stored in the library and searched in the searching of the library.

The library data may include shape information and axis information.

The alignment step may include performing the alignment by matching shape information and axis information, acquired from the scan data with shape information and axis information of the library data.

In an embodiment, a device for aligning a digital scanbody may include: a scan unit configured to acquire image data by scanning an oral structure including a structure; a control unit configured to perform data calculation by using the image data acquired through the scan unit and stored library data; and a display unit configured to display a scan process of the scan unit and an alignment process of the control unit.

The scan unit may be a handheld 3D scanner.

The control unit may include a library model selection unit configured to select library data from a plurality of library model data stored in a library, a scan data analysis unit configured to analyze information of the image data acquired through the scan unit, and a data matching unit configured to match and align the library data and the image data by comparing information of the library data and information of the image data.

The control unit may further include a reliability check unit configured to check the reliability of a corrected scanbody aligned by the data matching unit.

Advantageous Effects

The method for aligning a digital scanbody and the device using the same may generate an aligned digital scanbody by matching the scan data acquired in the image acquisition step with the shape information and axis information of the library data stored in the library.

Furthermore, the method and device may perform alignment on axes, height and directions by utilizing a plurality of axes and reference planes of a scanbody, thereby reducing an error of the scanbody and improving accuracy.

Furthermore, the location of the fixture may be easily checked through the digital scanbody, which makes it possible to improve the fabrication efficiency of an implant prosthesis and to provide a precise prosthesis to a patient.

Furthermore, before an actual prosthesis is fabricated, images may be coupled through the digital scanbody. Thus, the fastening state of a prosthesis may be checked to reduce unnecessary operations.

Furthermore, the reliability of the digital scanbody may be improved through the library data, which makes it possible to reduce the cost and operation time required for fabricating a prosthesis.

BRIEF DESCRIPTION OF DRAWINGS

FIGS. 2 and 3 are flowcharts illustrating a method for aligning a digital scanbody in accordance with an embodiment of the present disclosure.

FIG. 5 is a diagram illustrating that the library data stored in the library is divided into a plurality of categories, in the method for aligning a digital scanbody in accordance with the embodiment of the present disclosure.

FIG. 6 is a flowchart illustrating a method for aligning a digital scanbody in accordance with another embodiment of the present disclosure.

FIG. 7 is a schematic configuration diagram illustrating a device for aligning a digital scanbody in accordance with an embodiment of the present disclosure.

MODE FOR INVENTION

Figure 1:
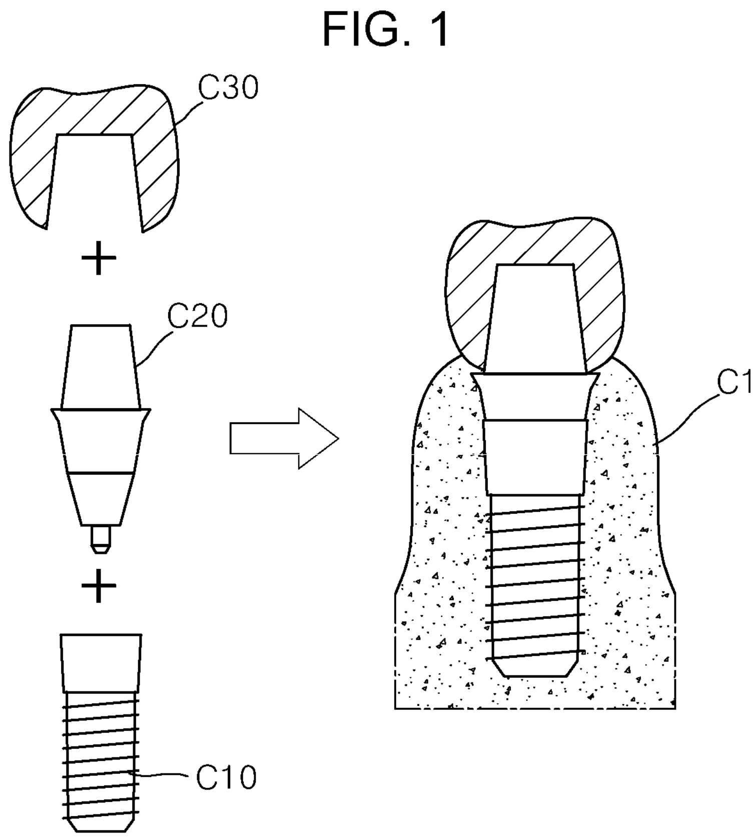
FIG. 1 is a diagram for describing the structure of an implant prosthesis in accordance with an embodiment of the present disclosure.

The advantages and characteristics of the present disclosure and a method for achieving the advantages and characteristics will be clearly understood through the following embodiments with reference to the accompanying drawings. However, the present disclosure may be embodied in different forms and should not be construed as being limited to the embodiments set forth herein. Rather, these embodiments are provided to make this disclosure thorough and complete, and fully convey the scope of the present disclosure to those skilled in the art. The present disclosure is only defined by the scope of claims. Throughout the specification, like reference numerals refer to the same elements.

Hereafter, the present disclosure will be described in detail with reference to the drawings.

FIG. 1 is a diagram for describing the structure of an implant prosthesis in accordance with an embodiment of the present disclosure.

As illustrated in FIG. 1, a tooth implant crown procedure indicates a procedure of providing a substituent capable of substituting a busted tooth in an oral cavity of a patient, when the busted tooth is removed (extracted) and thus lost. In other words, the tooth implant crow procedure indicates a procedure of implanting an artificially manufactured tooth to substitute a natural tooth.

A tooth implant crown may be roughly divided into three components. One of the components is a fixture C10 which is formed to have a screw shape on the outer circumferential surface thereof, and turned and fixed to a gum C1. The fixture C10 may be a structure corresponding to the root of a natural tooth, and firmly fixed to an alveolar bone. The fixture C10 may have a cavity formed therein in a direction facing the direction in which the fixture C10 is fixed toward the gum C1. The cavity formed in the fixture C10 may be coupled to an object having a protrusion corresponding to the cavity.

In order to fix an artificial tooth C30 to the fixture C10, a structure C20 is needed between the artificial tooth C30 and the fixture C10 inserted into the bone of the gum. The structure C20 is connected to the fixture C10 so as to be placed over the gum, and coupled to a prosthesis, i.e. the artificial tooth C30. At this time, the structure C20 may include both a ready-made product and a custom product. The ready-made product may indicate a structure which is previously manufactured according to the heights of the implanted fixture C10 and the gum, and the custom product may indicate a structure which is manufactured suitably for the shapes of the gum and tooth of each patient. The fixture C10, the structure C20 and the artificial tooth C30 may be all coupled to substitute a busted or removed tooth.

At this time, in order to couple the structure C20 and the artificial tooth C30 after the fixture C10 is implanted into the alveolar bone of the gum, the location of the fixture C10 needs to be checked. Furthermore, the artificial tooth 30 may have a different shape and size for each person, not a standardized shape, even though the artificial tooth 30 is implanted at the same location of each person. Furthermore, since the teeth function to chew and cut food through the occlusion between the upper and lower jaws, the direction of a tooth also serves as an important factor during a coupling process with the artificial tooth C30. For example, a certain person may have a back tooth on the left side of the lower jaw, but the area, height and direction of the back tooth may be different from those of a back tooth formed on the left side of the lower jaw of another person. Therefore, the height and direction (specifically, axis) of the artificial tooth C30 need to be decided according to the oral structure of each person, such that the artificial tooth C30 normally functions to make a patient feel comfortable.

In order to accomplish the above-described object, a scanbody or abutment corresponding to the structure C20 coupled to the fixture C10 may be fastened to the fixture C10, and the inside of the oral cavity may be scanned to check the oral structure. Since the scanbody or abutment may be fastened to make it easy to check the depth and direction of the implanted fixture C10, the implant location and direction of the implanted fixture C10 may be corrected before the artificial tooth C30 is coupled. Furthermore, the portion of the artificial tooth C30, coupled to the structure C20, may be processed to implement the height and direction of the artificial tooth C30, which are suitable for a patient.

Figure 2:
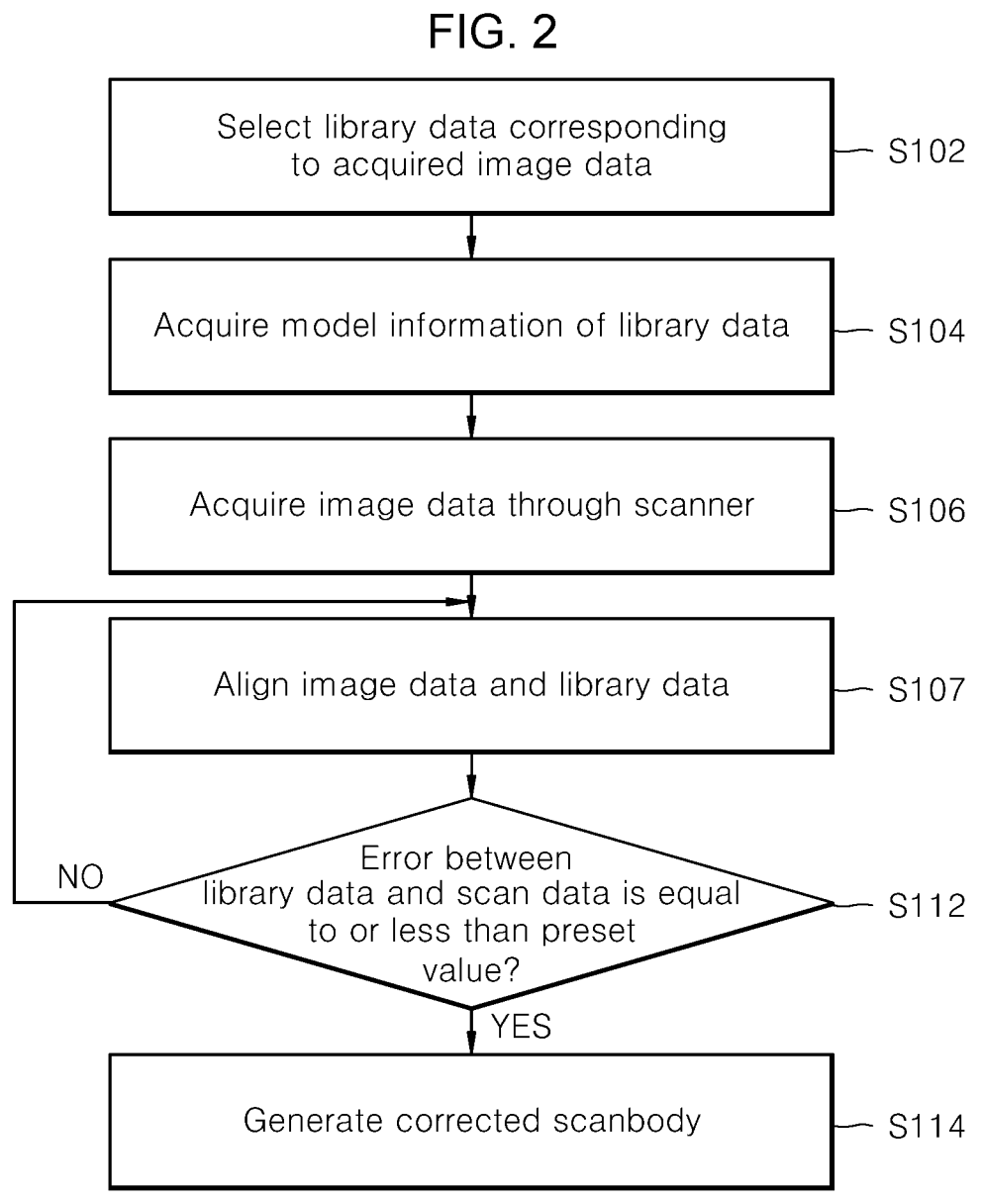
Figure 3:
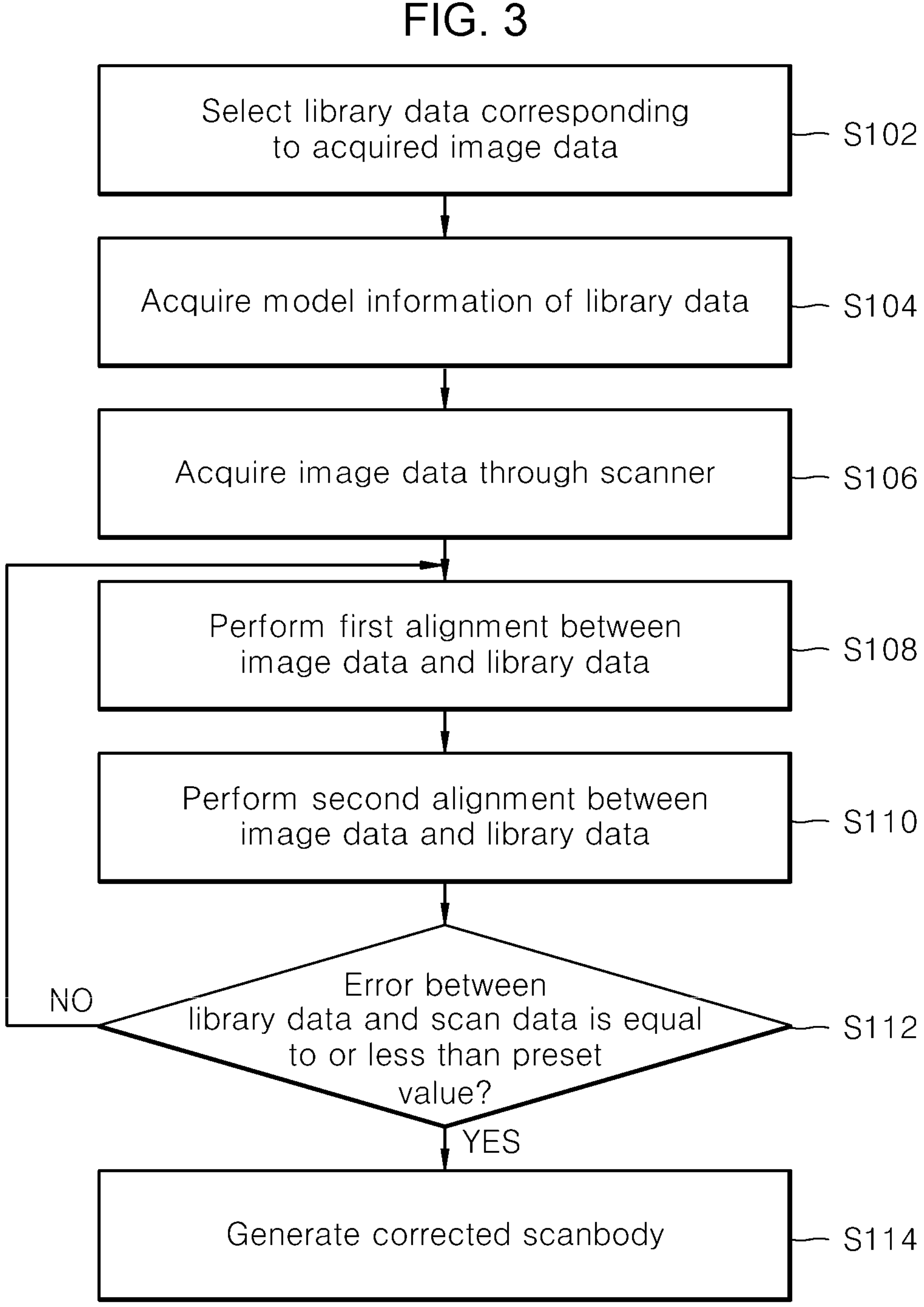

FIGS. 2 and 3 are flowcharts illustrating a method for aligning a digital scanbody in accordance with an embodiment of the present disclosure.

Referring to FIGS. 2 and 3, the method for aligning a digital scanbody in accordance with the embodiment of the present disclosure may include a data selection step S102 of selecting one or more library data among a plurality of library model data stored in a library and an image acquisition step S106 of acquiring image data by scanning an oral structure including a structure through a scanner.

A user may scan the oral structure of a patient through the scanner. At this time, the oral structure of the patient, i.e. a target object to be scanned through the scanner, may correspond to the actual oral cavity of the patient. If necessary, however, the oral structure may correspond to an impression model or plaster model acquired by performing impression taking on the inside of the oral cavity of the patient, by using a material such as alginate. According to the user's determination, a scan target suitable for applying the method for aligning a digital scanbody in accordance with the embodiment of the present disclosure may be selected and used.

Before the scan on the oral structure is performed, library data corresponding to a scanbody to be applied to the oral structure may be first selected. At this time, the library data may include one or more of a plurality of library model data stored in a data library included in an application or software in which the scan and the digital scanbody alignment in accordance with the embodiment of the present disclosure are performed. Digital data (library model data) on prostheses required for an oral remedy of a patient may be stored in the data library. The stored library model data may be data on an abutment or scanbody which can be implanted into the oral cavity of the patient. As such, the library model data on the abutment or scanbody may be utilized to check the depth and direction of the fixture C10 described with reference to FIG. 1. Desirably, the structure may be a scanbody. As the scanbody is implanted, the depth and direction of the fixture may be checked through the height and direction of the scanbody. The library model data stored in the library may be three-dimensional (3D) CAD plan data of the structure or 3D surface data obtained by converting plan data.

When the user selects library data, which the user wants to use, from the plurality of library model data and assigns the selected library data, the selected library data is arranged at a random location on a user interface (not illustrated). At this time, the user interface may be a scan interface on which the image data acquired by scanning the scan target through the scanner is displayed. The library model data stored in the library may each include shape information and axis information.

Figure 4:
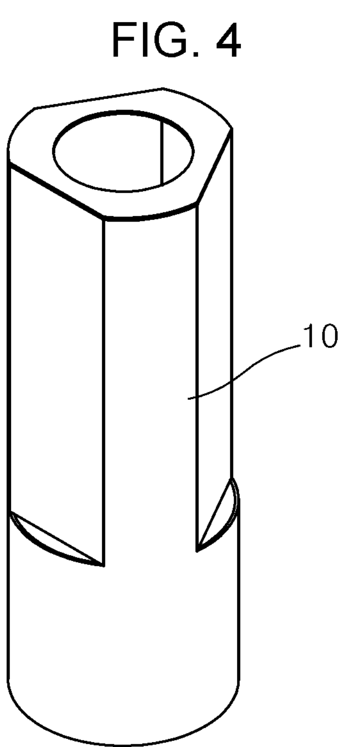
FIG. 4 is a diagram illustrating library data stored in a library in the method for aligning a digital scanbody in accordance with the embodiment of the present disclosure.
Figure 5:
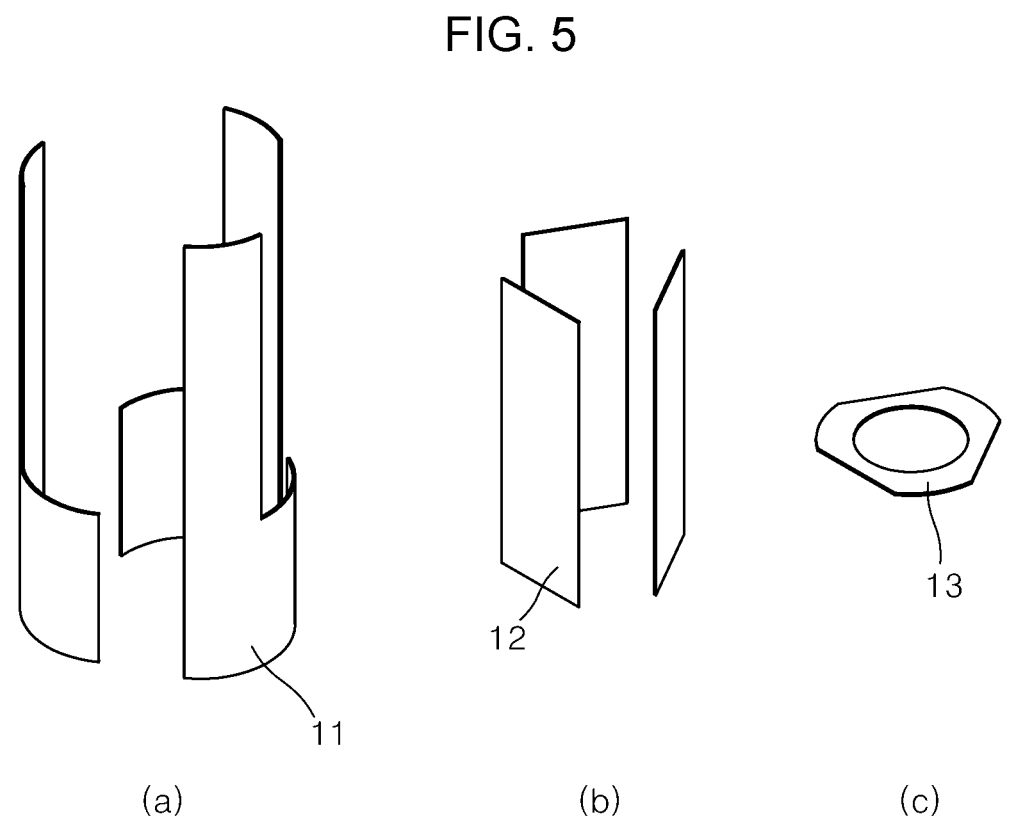

FIG. 4 is a diagram illustrating library data stored in a library in the method for aligning a digital scanbody in accordance with the embodiment of the present disclosure, and FIG. 5 is a diagram illustrating that the library data stored in the library is divided into a plurality of categories, in the method for aligning a digital scanbody in accordance with the embodiment of the present disclosure.

Referring to FIGS. 4 and 5, library data 10 may be an abutment or scanbody, and expressed as the 3D shape of the abutment or scanbody. The 3D shape may have information on the shape of a plane, the shape of a curved plane, and a virtual axis passing through the center of each of the shapes. Depending on the shapes, the library data 10 may be classified. Referring to FIG. 4, the library data 10 may be divided and categorized into first data 11 having a curved shape, second data 12 having a rectangular plane shape, and third data 13 corresponding to a polygonal top surface of the library data 10 and having a hole formed in the center thereof, and the data 11 to 13 may be processed to have model information including shape information and axial information. In this way, the model information of the library data may be acquired in step S104. The acquired model information as well as information acquired from scan data may be used for an alignment step S107 or a second alignment step S110, which will be described below.

The user scans the inside of the oral cavity including the structure in the image acquisition step S106. Data acquired through the scan may be two-dimensional (2D) image data or 3D volume data whose depth can be determined through the acquired 2D image data and which is formed by emitting special light. Desirably, the image data formed on the scan interface through the 3D scan in the image acquisition step S106 may become 3D volume data (scan data) in a voxel shape having a volume.

As the 3D scanner for acquiring 3D volume data, a table scanner may be used, which acquires scan data by rotating a tray in which an impression taking model or plaster model for the inside of the oral cavity is arranged. Alternatively, as the 3D scanner, a handheld scanner may be used, which is held by a user's hand and directed to the inside of the oral cavity to receive light reflected from the inside of the oral cavity, and acquires the received light as 3D scan data.

After the image data is acquired through the scanner, the image data and the library data may be aligned through the alignment step S107. The alignment step S107 may include aligning the image data and the library data by using one or more algorithms for aligning the image data and the library data. As the algorithm used in the alignment step S107, a best-fit algorithm may be used to align the image data and the library data. The best-fit algorithm may indicate an algorithm that minimizes a deviation error by adjusting the location of a target to be aligned, by using a deviation minimization option. Alternatively, the alignment step S107 may include aligning the image data and the library data by comparing and matching the shape information and axis information of the image data with those of the library data.

In the method for aligning a digital scanbody in accordance with the embodiment of the present disclosure, the alignment step S107 may include two or more sub alignment steps. As illustrated in FIG. 3, the image data and the library data may be aligned through a first alignment step S108, after the image data is acquired through the scanner. As the alignment method used in the first alignment step S108, one or more of various alignment methods suitable for data matching may be selectively used. However, the best-fit algorithm, which minimizes a deviation error by adjusting the location of a target to be aligned, by using a deviation minimization option, may be used to align the image data and the library data. As the first alignment step S108 is performed, the library data arranged randomly on the scan interface may be rapidly aligned with the scan data. At this time, since that the location of the structure (e.g. the abutment or scanbody), acquired through the scan data, is close to an actual implant location due to the characteristic of the scan data, the library data may be horizontally moved and rotated on the basis of the scan data, in order to perform data matching.

However, even when the best-fit algorithm is used to perform data alignment, a scan error might already occur during the scan process for acquiring the scan data, and no weight is given to the axis information or rotation direction which is important information of the scanbody, while the first alignment step S108 is performed. Therefore, overall errors may be reduced, but the data may be aligned while distortion such as rotation or lean remains. In this case, additional alignment may need to be performed in order to secure precision required for providing an actual prosthesis.

In order to secure the above-described precision, the method for aligning a digital scanbody in accordance with the embodiment of the present disclosure may further include the second alignment step S110 of aligning the image data and the library data by using an alignment algorithm different from that of the first alignment step S108. In the second alignment step S110, model information including the shape information and axis information of the library data arranged on the scan interface may be used. Such model information may be geometrical information whose shape is divided through a plurality of categories as illustrated in FIG. 4, and which includes information on the center point, axis and plane of each shape. Since the scan data acquired through the image acquisition step S106 also has geometrical information including the shape information and axis information of the structure, additional alignment may be performed to match the geometrical information of the library data with the geometrical information of the scan data.

In the second alignment step S110, the data 11 to 13 obtained by the library data 10 through divided categories may be sequentially aligned. For example, after the first alignment step S108 is performed through the best-fit algorithm, the first data 11 having a curved shape corresponding to a portion of a side surface of the library data 10 may be aligned with the scan data, such that the shape information and axis information of the first data 11 correspond to those of the scan data. Then, the second data 12 having a plane shape corresponding to the other portion of the side surface of the library data 10, different from the first data 11, may be aligned with the scan data such that the shape information and axis information of the second data 12 correspond to those of the scan data. Finally, the third data 13 corresponding to the top surface of the library data 10 may be aligned with the scan data such that the shape information and axis information of the third data 13 correspond to those of the scan data.

According to another method, the first data 11 may have information on the central axis of the library data 10, and the second data 12 may have information on the direction of the library data 10. That is because the structure of the scan data, corresponding to the target of the scan, is not a complete rotation body, but may have a region which is formed on the surface of the structure so as to indicate the direction of the structure. For example, the region may correspond to the above-described data having a rectangular plane shape. In addition, the third data 13 may have information on the height of the library data 10. At this time, the second alignment step S110 may include initially aligning the first data 11 and the scan data by comparing the central axes of the first data 11 and the scan data. The central axis of the cylindrical portion of the scan data may be set to the central axis of the scan data, and then compared and aligned with the central axis of the first data 11. Furthermore, the heights of the third data 13 and the scan data may be compared and aligned with each other. The height of a plane corresponding to the top of the scan data may be set to the height of the scan data, and then compared and aligned with the height of the third data 13. Furthermore, the directions of the second data 12 and the scan data may be compared and aligned with each other. The direction of a portion of the side surface of the scan data, corresponding to the plane, may be set to the direction of the scan data, and then compared and aligned with the direction of the second data 12. When the second alignment step S110 is performed through such a method, the precision of the data may be improved through the additional alignment using the shape information and axis information including the central axes, the heights and the directions, along with the first alignment step S108 of reducing overall errors.

In the present embodiment, it has been described that the central axis of the first data, the height of the third data and the direction of the second data are sequentially compared and aligned with the information of the scan data. However, this is only an example, and the order in which the data are compared and aligned may be changed. Furthermore, the number of categories for dividing the data is not limited to three, but set to such a value that the data has one or more pieces of shape information and axis information according to the shape of the structure, in order to express various reference directions, reference axes, reference heights and the like. For example, the scan data including the structure may be formed to have information on the central axis, the height and the direction within one category. In this case, the library data and the scan data may be aligned through the single category. Similarly, all of the central axes, heights and directions of the library data and the scan data need not be used for alignment, and a comparison and alignment step may be added or removed to such an extent that a prosthesis can be precisely and rapidly provided.

Furthermore, even when the shape information and the axis information are separated to perform alignment in the above-described alignment step S107, the alignment may be performed through the same alignment method as the second alignment step S110. For example, the central axes of the image data and the library data may be initially compared and aligned. Then, shape information (direction or height information) other than the axis information may be used to perform alignment, with the central axes of the image data and the library data aligned with each other. By performing the alignment using the shape information and the axis information, it is possible to decide the alignment location and direction of the library data corresponding to the actual scan image data, thereby improving the reliability of the data. The present disclosure is not limited to the order in which the alignment through the axis information is first performed and the alignment through the shape information is then performed, but the order of the information used for the alignment may be changed.

When the second alignment step S110 is completed, errors of the library data and the scan data may be compared to check the reliability of the data, in step S112. The reliability of the data may be checked by comparing the errors of the respective data, and calculated in consideration of the sum of error values and the ratio of data in which errors occurred.

The reliability of the data may be checked by determining whether an error is lower than a reference value preset in an application or software. When the error exceeds the preset value, the additional alignment step may be performed again, or an operation of outputting a message may be performed, the message instructing a user to perform an addition scan because it was determined that distortion occurred due to an input of wrong scan data. When an error is equal to or lower than the preset value, it may be determined that the library data and the scan data have been satisfactorily aligned with each other. In this case, the alignment process may be ended, and a corrected scanbody may be generated by coupling the library data and the scan data on the basis of the aligned data, in step S114. The corrected scanbody may be generated to correct insufficiently scanned data of the scan data. As a result, the reliability of the data may be improved through the correction of the scan data based on the library data, which makes it possible to provide a more precise prosthesis to a patient.

Hereafter, a method for aligning a digital scanbody in accordance with another embodiment of the present disclosure will be described in detail. However, the contents of the present embodiment, overlapping the above-described contents, will be briefly described or omitted.

Figure 6:
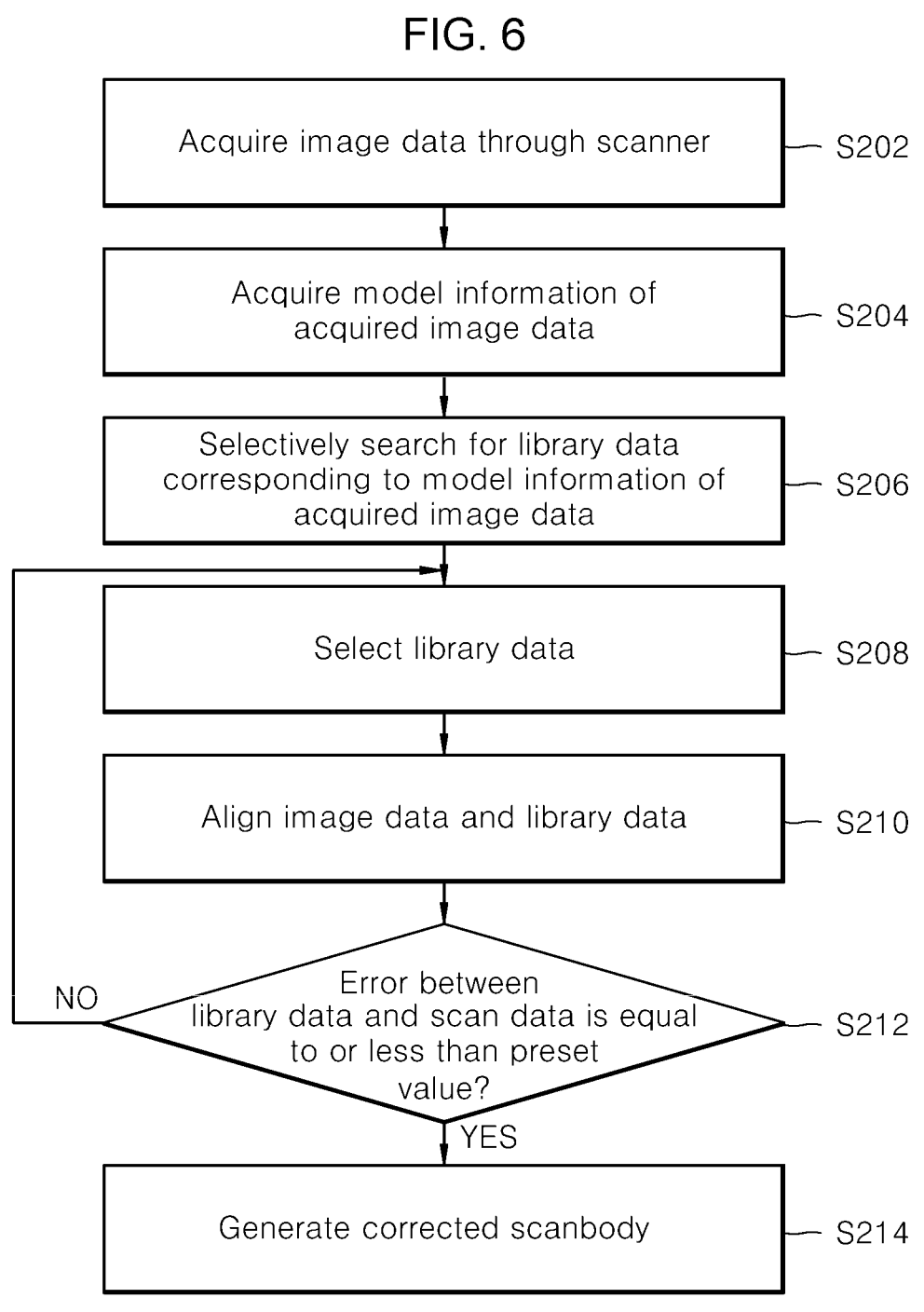

FIG. 6 is a flowchart illustrating a method for aligning a digital scanbody in accordance with another embodiment of the present disclosure.

Referring to FIG. 6, the method for aligning a digital scanbody in accordance with another embodiment of the present disclosure may include an image acquisition step S202 of acquiring image data by scanning an oral structure including a structure through a scanner and a selection step S208 of selecting one or more library data among a plurality of library model data stored in a library.

The image acquisition step S202 may be performed to acquire image data on the inside of the oral structure through the scanner, and the image data may be displayed as 3D volume data on a scan interface. When the scan is performed on the oral structure including the structure, model information on the structure may be acquired together in step S204. At this time, the model information on the structure may include the shape information and axis information of the structure. More specifically, the model information on the structure may include the central axis, height and direction of the structure. The model information of the scan data including the structure may be used for data alignment in an alignment step S210 which will be described below.

Through the model information acquired for the scan data including the structure, library data corresponding to the acquired model information may be selectively searched in step S206. Referring to FIGS. 4 and 5, library data 10 may include first data 11 formed in a cylindrical shape and having central axis information, second data 12 formed in a plane shape and having direction information, and third data 13 formed in a polygonal shape and having height information as in the above-described embodiment. Software may search for a plurality of library model data corresponding to one or more pieces of information among plural pieces of model information acquired from the scan data (e.g. axis information and shape information including central axis information, height information and direction information). In this case, a user may rapidly select and apply library data, which the user wants to apply, without checking all of the library model data stored in the data library.

The user may select library data, which the user wants to apply, among the plurality of library model data searched through the library search step S206, in step S208. The selected data may have model information including shape information and axis information, and the model information may be divided into a plurality of categories. The configuration in which the model information of the library data may be divided into the plurality of categories has been already described above.

When the user selects the library data, the alignment step S210 of aligning the scan data corresponding to the image data with the selected library data may be performed. At this time, the alignment step S210 may correspond to the second alignment step S110 in the above-described embodiment. The alignment step S210 may include aligning the library data and the scan data by matching the shape information and axis information acquired through the library data with those acquired through the scan data. For example, the central axis of the scan data and the central axis of the first data 11 may be compared and aligned, the height of the scan data and the height of the third data 13 may be compared and aligned, and the direction of the scan data and the direction of the second data 12 may be compared and aligned. As described above, however, the comparison and alignment process need not to be performed in order of the first data 11, the third data and the second data 12, and a proper order and comparison items may be selected in order to improve the reliability of the data and to rapidly form the data.

The method for aligning a digital scanbody in accordance with another embodiment of the present disclosure may also further include a reliability check step S212 of determining whether an error between the library data and the scan data is equal to or less than a preset value, after the alignment step S210 is performed. In the reliability check step, the reliability may be calculated on the basis on the sum of errors in all of the data, or calculated in consideration of the sum of errors and an error rate. When the error between the library data and the scan data exceeds a preset value on a program or application in the reliability check step, it may be determined that an error occurred in the selection of the library data. In this case, library data corresponding to the scan data may be selected again to perform alignment. Alternatively, it may be determined that an element (e.g. the central axis, height or direction) of the model information, required for performing the alignment step S210, was not sufficiently reflected. In this case, an additional element may be considered to perform additional alignment. For example, when only the central axis alignment is performed in the initial alignment step S210 and the error exceeds the preset value in the reliability check step S212, the direction alignment may be additionally performed.

Alternatively, since the scan data might have been distorted by an insufficient scan on the inside of the oral cavity including the structure, an operation of outputting a message may be performed, the message instructing the user to perform an additional scan. When an error is equal to or lower than the preset value, it may be determined that the library data and the scan data have been satisfactorily aligned with each other. In this case, the alignment process may be ended, and a corrected scanbody may be generated by coupling the library data and the scan data on the basis of the aligned data, in step S214. The generation of the corrected scanbody may correct insufficiently scanned data of the scan data. As a result, the reliability of the data may be improved through the correction of the scan data based on the library data, which makes it possible to provide a more precise prosthesis to a patient.

Hereafter, a device for aligning a digital scanbody (hereafter, referred to as a digital scanbody alignment device) in accordance with an embodiment of the present disclosure will be described.

Figure 7:
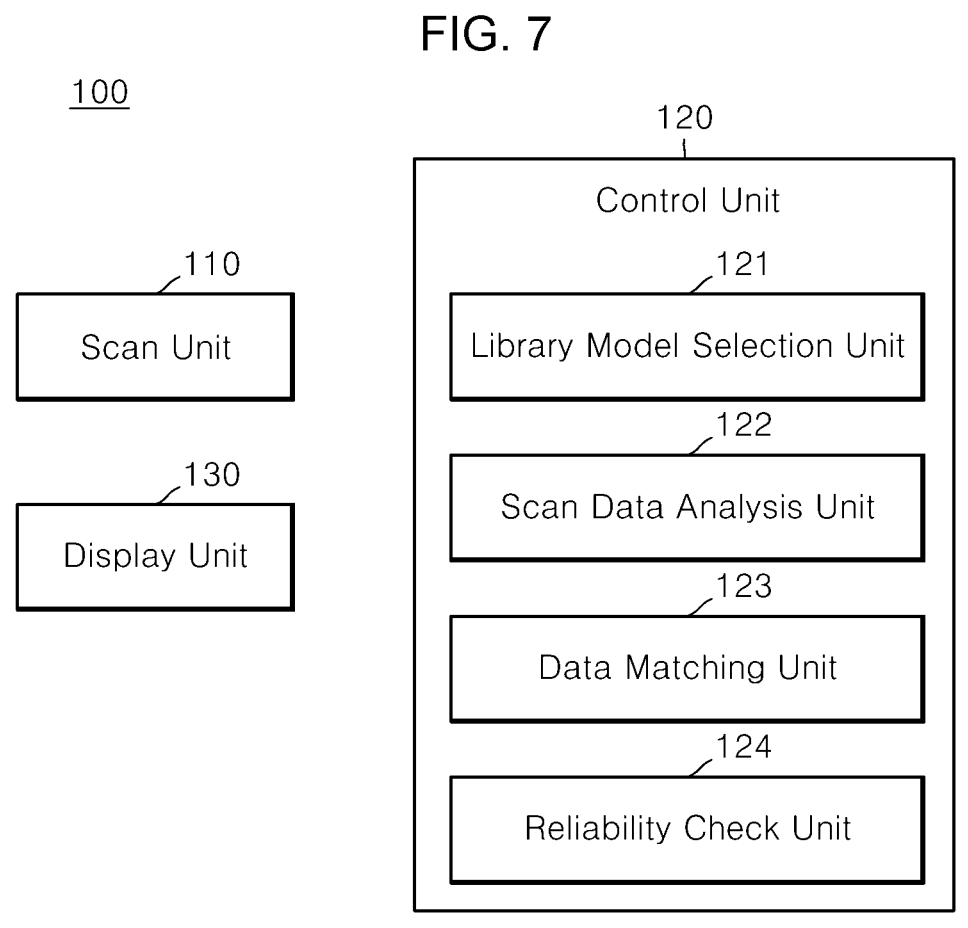

FIG. 7 is a schematic configuration diagram illustrating a digital scanbody alignment device in accordance with an embodiment of the present disclosure.

Referring to FIG. 7, a digital scanbody alignment device 100 in accordance with an embodiment of the present disclosure may include a scan unit 110 configured to acquire image data by scanning an oral structure including a structure and a control unit 120 configured to perform a data calculation operation using the image data acquired through the scan unit 110 and stored library data. The digital scanbody alignment device 100 refers to a device that aligns scan data acquired through 3D scanning with library data, in order to further improve the data reliability of the scan data. The scan unit 110 included in the digital scanbody alignment device 100 may scan the inside of an actual oral cavity of a patient or an oral cavity model for the oral structure of the patient, including the structure corresponding to a real thing, in order to perform an alignment process. At this time, the scan unit 110 may be a handheld 3D scanner which is used in the above-described method for aligning a digital scanbody, and the user may freely scan the oral structure including the structure at a desired distance and angle.

The control unit 120 includes a library model selection unit 121 configured to select library data, corresponding to the structure set to a scan target, from a plurality of library model data stored in a scan application or software. At this time, the selecting of the library data may indicate that a user who uses the digital scanbody alignment device in accordance with the embodiment of the present disclosure directly selects library data corresponding to the scan target from a data library, if necessary, or library model data corresponding to the data acquired through the scan performed by the scan unit 110 are selectively searched and selected. The data library may have 3D CAD model information on an abutment or scanbody corresponding to the structure which is to be implanted into the oral cavity. Furthermore, the library data may have shape information and axis information on the corresponding data. When the library data to be used is selected through the library model selection unit, the selected library data and the scan image data may be aligned.

The control unit 120 may include a scan data analysis unit 122 configured to analyze the information of the image data acquired through the scan unit 110. The scan data analysis unit 122 may acquire the shape information and axis information of the structure from the acquired image data, and the acquired shape information and axis information may be used for data matching.

The control unit 120 may further include a data matching unit 123. The data matching unit 123 may compare the library data selected by the library model selection unit 121 to the information of the image data, required for the alignment by the scan data analysis unit 122, on the basis of the image data acquired by the scan unit 110. As the data matching unit 123 performs the matching and alignment by comparing the information of the library data and the information of the image data, the library data may make up for the imperfection of the image data acquired by the scan unit 110. At this time, the best-fit algorithm or an algorithm for comparing and matching the central axis information, height information and direction information of the library data with those of the image data may be used as the algorithm used for the matching and alignment of the data matching unit 123. Alternatively, the best-fit algorithm may be first used to perform alignment, and the shape information and axis information (central axis, height and direction) of the image data and the library data may be additionally used to perform alignment, in order to improve the reliability of the data. The alignment process using the shape information and the axis information has been already described above.

The control unit 120 may include a reliability check unit 124 configured to check the reliability of a corrected scanbody which is formed after the alignment is performed by the data matching unit 123. The reliability check unit 124 may determine whether an error between the image data and the library data falls within a preset range. When the error exceeds the preset range, the data matching unit 123 may perform additional alignment. When the error is equal to or less than the preset range, the corrected scanbody may be formed as one data, which makes it possible to provide a precise prosthesis to a patient.

The above description is simply given for illustratively describing the technical spirit of the present disclosure, and those skilled in the art to which the present disclosure pertains will appreciate that various modifications and changes are possible without departing from the essential characteristic of the present disclosure.

Accordingly, the embodiments disclosed in the present disclosure are intended not to limit but to describe the technical spirit of the present disclosure, and the scope of the technical spirit of the present disclosure is not limited by the embodiments. The scope of the present disclosure shall be interpreted on the basis of the following claims, and it shall be interpreted that all the technical spirit within the scope equivalent thereto falls within the scope of the present disclosure.

INDUSTRIAL APPLICABILITY

The present disclosure provides a method for aligning a digital scanbody, which acquires precise corrected scanbody data by aligning image data acquired through a 3D scanner with library data stored in a library by using the information of the image data and the library data, and a device using the same.

The invention claimed is:

1. A method for aligning a digital scanbody, comprising:

a library data selection step of selecting one or more library data among a plurality of library model data stored in a library by a control unit;

an image acquisition step of acquiring image data by scanning an oral structure including a structure through a scanner; and an alignment step of aligning the image data and the library data by the control unit, wherein in the alignment step, the structure in the image data and the library data is matched and aligned based on at least one of central axis, direction, and height of the library data, wherein a corrected scanbody is generated to correct insufficiently scanned data of scan data included in the image data, by coupling the library data and the scan data, and wherein the library data have information of the central axis and information of the height based on a curved shape and a top surface shape.

2. The method of claim 1, wherein the image data acquired in the image acquisition step is three-dimensional (3D) scan data acquired through the scan.

3. The method of claim 1, wherein the library data is data on a scanbody which is to be implanted into an oral cavity.

4. The method of claim 1, wherein the alignment step comprises aligning the image data and the library data by using a best-fit algorithm.

5. The method of claim 1, wherein the alignment step comprises performing the alignment by matching shape information and axis information of the scan data on the structure, acquired in the image acquisition step, with shape information and axis information of the library data.

6. The method of claim 1, wherein the alignment step comprises one or more alignment steps.

7. The method of claim 6, wherein the alignment step comprises a first alignment step of aligning the image data and the library data by using a best-fit algorithm.

8. The method of claim 7, wherein the alignment step further comprises a second alignment step of aligning the image data and the library data by using an algorithm different from the first alignment step.

9. The method of claim 8, wherein the second alignment step comprises performing additional alignment by matching shape information and axis information of the scan data on the structure, acquired in the image acquisition step, with shape information and axis information of the library data.

10. The method of claim 9, further comprising a reliability check step of determining whether an error between the library data and the scan data acquired from the image data is equal to or less than a preset value, after the second alignment step.

11. The method of claim 10, wherein the reliability check step comprises performing additional alignment when the error between the library data and the scan data exceeds the preset value, and generating the corrected scan body on the basis of the aligned data when the error between the library data and the scan data is equal to or less than the preset value.

12. A method for aligning a digital scanbody, comprising:

an image acquisition step of acquiring image data by scanning an oral structure including a structure through a scanner;

a data selection step of selecting one or more library data among a plurality of library model data stored in a library by a control unit; and an alignment step of aligning the image data and the library data by the control unit, wherein in the alignment step, the structure in the image data and the library data is matched and aligned based on at least one of central axis, direction, and height of the library data, wherein a corrected scanbody is generated to correct insufficiently scanned data of scan data included in the image data, by coupling the library data and the scan data, and wherein the library data have information of the central axis and information of the height based on a curved shape and a top surface shape.

13. The method of claim 12, wherein model information including shape information and axis information is acquired from the scan data on the structure, acquired in the image acquisition step.

14. The method of claim 13, further comprising selectively searching for library data corresponding to the model information on the structure.

15. The method of claim 14, further comprising selecting one or more library data among a plurality of library model data stored in the library and searched in the searching of the library.

16. The method of claim 15, wherein the library data comprises shape information and axis information.

17. The method of claim 16, wherein the alignment step comprises performing the alignment by matching shape information and axis information, acquired from the scan data with shape information and axis information of the library data.

18. A device for aligning a digital scanbody, comprising:

a scan unit configured to acquire image data by scanning an oral structure including a structure;

a control unit configured to perform data calculation by using the image data acquired through the scan unit and stored library data; and a display unit configured to display a scan process of the scan unit and an alignment process of the control unit, wherein the control unit is configured to match and align the structure in the image data and the library data based on at least one of central axis, direction, and height of the library data, wherein a corrected scanbody is generated to correct insufficiently scanned data of scan data included in the image data, by coupling the library data and the scan data, and wherein the library data have information of the central axis and information of the height based on a curved shape and a top surface shape.

19. The device of claim 18, wherein the scan unit is a handheld 3D scanner.

20. The device of claim 18, wherein the control unit comprises a library model selection unit configured to select library data from a plurality of library model data stored in a library, a scan data analysis unit configured to analyze information of the image data acquired through the scan unit, and a data matching unit configured to match and align the library data and the image data by comparing information of the library data and information of the image data.

21. The device of claim 18, wherein the control unit further comprises a reliability check unit configured to check the reliability of a corrected scanbody aligned by the data matching unit.

* * * * *